United States Patent [19]

Simandl et al.

[11] Patent Number: 5,976,471
[45] Date of Patent: Nov. 2, 1999

[54] OZONE DECOMPOSING FILTER

[75] Inventors: Ronald F. Simandl, Farragut; John D. Brown, Harriman, both of Tenn.; LeRoy L. Whinnery, Jr., Dublin, Calif.

[73] Assignee: Lockheed Martin Energy Systems, Inc., Oak Ridge, Tenn.

[21] Appl. No.: 08/838,294

[22] Filed: Apr. 16, 1997

[51] Int. Cl.$^6$ ...................................................... A62B 11/00
[52] U.S. Cl. ........................ 422/122; 422/168; 422/171; 55/527; 55/528; 428/113; 428/131
[58] Field of Search ..................................... 422/168–171, 422/120, 122; 428/131, 113, 105; 55/528, 527; 96/16, 224, 226

[56] References Cited

U.S. PATENT DOCUMENTS

| | | | |
|---|---|---|---|
| 4,366,085 | 12/1982 | Ikegami et al. | 423/219 |
| 5,160,586 | 11/1992 | Yoshimoto et al. | 502/20 |
| 5,256,377 | 10/1993 | Nakamaru | 422/122 |

*Primary Examiner*—Hien Tran
*Attorney, Agent, or Firm*—J. Kenneth Davis

[57] ABSTRACT

In an improved ozone decomposing air filter carbon fibers are held together with a carbonized binder in a perforated structure. The structure is made by combining rayon fibers with gelatin, forming the mixture in a mold, freeze-drying, and vacuum baking.

4 Claims, 3 Drawing Sheets

30×

100×

OZONE DECOMPOSING FILTER

The U.S. Government has rights in this invention pursuant to contract no. DE-AC05-84OR21400 between the U.S. Department of Energy and Lockheed Martin Energy Systems, Inc.

FIELD OF THE INVENTION

The invention described herein relates generally to air filters, and more specifically to filters for removing ozone ($O_3$) from air or for converting ozone in air to normal oxygen ($O_2$).

BACKGROUND OF THE INVENTION

Frequently in crowded urban office environments, volatile air-borne contaminants contribute to a variety of undesirable effects on persons and property, collectively sometimes referred to as "sick building syndrome". These contaminants issue from various synthetic building materials, from contaminated heating, ventilation, and air conditioning ducts, and from a variety of electrical and electronic devices. A frequent and significant contributor to air contamination, and thus to "sick building syndrome" is ozone. Ozone is a very active form of oxygen molecule, and is produced in office buildings by electronic copiers, laser jet printers, and other electrical and electronic equipment. It is also produced by devices which use ultraviolet light, often for sterilization of medical and dental instruments, sterilization of deionized process water, sterilization of equipment used for hair care and other applications in cosmetology and skin care, and for surface activation of polymers and other manufacturing processes.

Ozone is a toxic gas that has an unpleasant, pungent odor that is detectable at concentrations as low as 0.05 parts per million (ppm). It becomes irritating to the eyes, nose, and lungs at about 0.1 ppm. The American Conference of Governmental and Industrial Hygienists (ACGIH) and the Occupational Safety and Health Administration (OSHA) have extablished the maximum permissible average concentration of ozone as 0.1 ppm over an eight hour exposure period.

Conventional methods for reducing ozone concentrations in air use activated carbon alone or in combination with metal catalysts or oxide catalysts such as activated manganese dioxide and high surface area ferric oxide. Examples of activated carbon filters that are available commercially are the "TAK Filter 800 Cell" produced by Roki Company in Tokyo, Japan, and a honeycomb activated carbon filter produced by Ricoh Co. in West Caldwell, New Jersey. These activated filters have been found to lose approximately one half their ozone decomposing capacity after about 1 days' service. U.S. Pat. No. 5,256,377 entitled "Ozone Decomposing Material and Ozone Decomposing Apparatus Using the Ozone Decomposing Material", issued Oct. 26, 1993 discusses this degradation issue. To overcome the loss of ozone decomposing capacity this patent claims the use of a number of dipentene compounds in combination with an activated carbon filter.

Because conventional air filters for reducing ozone made of activated carbon alone or with catalysts lose approximately one half their ozone decomposing capacity after just one day in service, and because these filters cost approximately $100 for one of a size suitable for an office copier or printer, an effort was undertaken to find or produce an ozone decomposing filter which is effective at decomposing ozone over a much longer period and at a greatly reduced cost. The present invention arose from that effort.

The present invention is a monolithic carbon composite filter and a simple, inexpensive method for producing it. The filter has been tested for ozone destroying capacity and has been found to be extremely effective. Moreover, this filter has a long ozone-decomposing lifetime without the use of catalysts or adsorbed dipentenes. Precursor materials are inexpensive, non-hazardous, and readily available. The method permits easy casting-to-shape of a monolithic filter.

OBJECTS OF THE INVENTION

Accordingly, it is an object of the present invention to provide a new and improved air filter which removes ozone from air or converts ozone to normal oxygen.

It is another object to provide a new and improved air filter for removing ozone from air or for converting ozone in air to normal oxygen which can be manufactured easily and inexpensively.

It is yet another object to provide a method for making a new and improved air filter which removes ozone from air or converts ozone to normal oxygen.

Further and other objects of the present invention will become apparent from the description contained herein.

SUMMARY OF THE INVENTION

In accordance with one aspect of the present invention, the foregoing and other objects are achieved by a filter for decomposing ozone which comprises a body which comprises between about 20 wt % and about 80 wt % carbonized cellulosic fibers and between about 80 wt % and about 20 wt % carbonized gelatin.

In accordance with a second aspect of the present invention, the foregoing and other objects are achieved by a method for making an ozone decomposing filter which comprises the steps of: combining gelatin, propylene glycol, and water to form a first mixture at sufficient temperature to dissolve the gelatin; combining tannic acid and carbonized cellulose fibers with the first mixture to form a second mixture; cooling the second mixture sufficiently for the second mixture to gell, forming a raw filter material; soaking the raw filter material in a mixture of methanol and glutaraldehyde sufficiently to reduce the propylene glycol and water content of the raw filter material and to cross-link the gelatin; removing methanol from the raw filter material by exposing the raw filter material to supercritical carbon dioxide; drying the raw filter material; curing and stabilizing the raw filter material in air by raising the temperature slowly until the raw filter material becomes dark brown in color; removing the continuous surface skin from the raw filter material; and carbonizing the raw filter material by heating in an inert atmosphere to form an ozone decomposing filter.

In accordance with a third aspect of the present invention, the foregoing and other objects are achieved by a method for making an ozone decomposing filter which comprises the steps of: combining gelatin, lithium bromide, and water to form a first mixture at sufficient temperature to dissolve the gelatin; combining tannic acid and carbonized cellulose fibers with the first mixture to form a second mixture; cooling the second mixture sufficiently for the mixture of water and glutaraldehyde sufficiently to reduce the propylene glycol content of the raw filter material and to cross-link the gelatin; heating the raw filter material to 100° C. in water and glutaraldehyde to complete the cross-linking; freeze-drying the raw filter material; curing and stabilizing the raw filter material in air by raising the temperature slowly until the raw filter material becomes dark brown in color; removing the continuous surface skin from the raw filter material; and carbonizing the raw filter material by heating in an inert atmosphere to form an ozone decomposing filter.

DETAILED DESCRIPTION OF THE INVENTION

The present invention comprises carbon fibers held together with a carbonized binder. The composite ozone decomposing filter is made by combining rayon fibers with gelatin, forming the mixture in a mold, freeze-drying, and vacuum baking. The ozone decomposing filter has a perforated structure that allows for adequate air flow through the ozone decomposing filter and for intimate contact of the ozone-laden air with the activated ozone decomposing filter. This composite ozone decomposing filter is normally activated to several hundred square meters per gram surface area prior to use and maintains this activation well during shipping and shelf storage.

Preferably, an ozone decomposing filter comprises from 20 to 80 wt % inexpensive carbonized cellulosic (rayon) fibers bound together with from 80 to 20 wt % of carbonized gelatin. The carbon fibers drastically reduce shrinkage of the fiter during further processing and carbonization of the binder. The carbon fibers also provide for an optimum average pore size in the finished carbon filter for mazimum ozone/air contact and subsequent ozone reduction.

To make the filter, from 2 to 30 parts per hundred weight of solvent (phs) of gelatin is dissolved in about 90° C. water to form a first mixture, and about 15 phs carbonized cellulose (rayon) fibers are added to the first mixture to form a second mixture.

Figure 1:
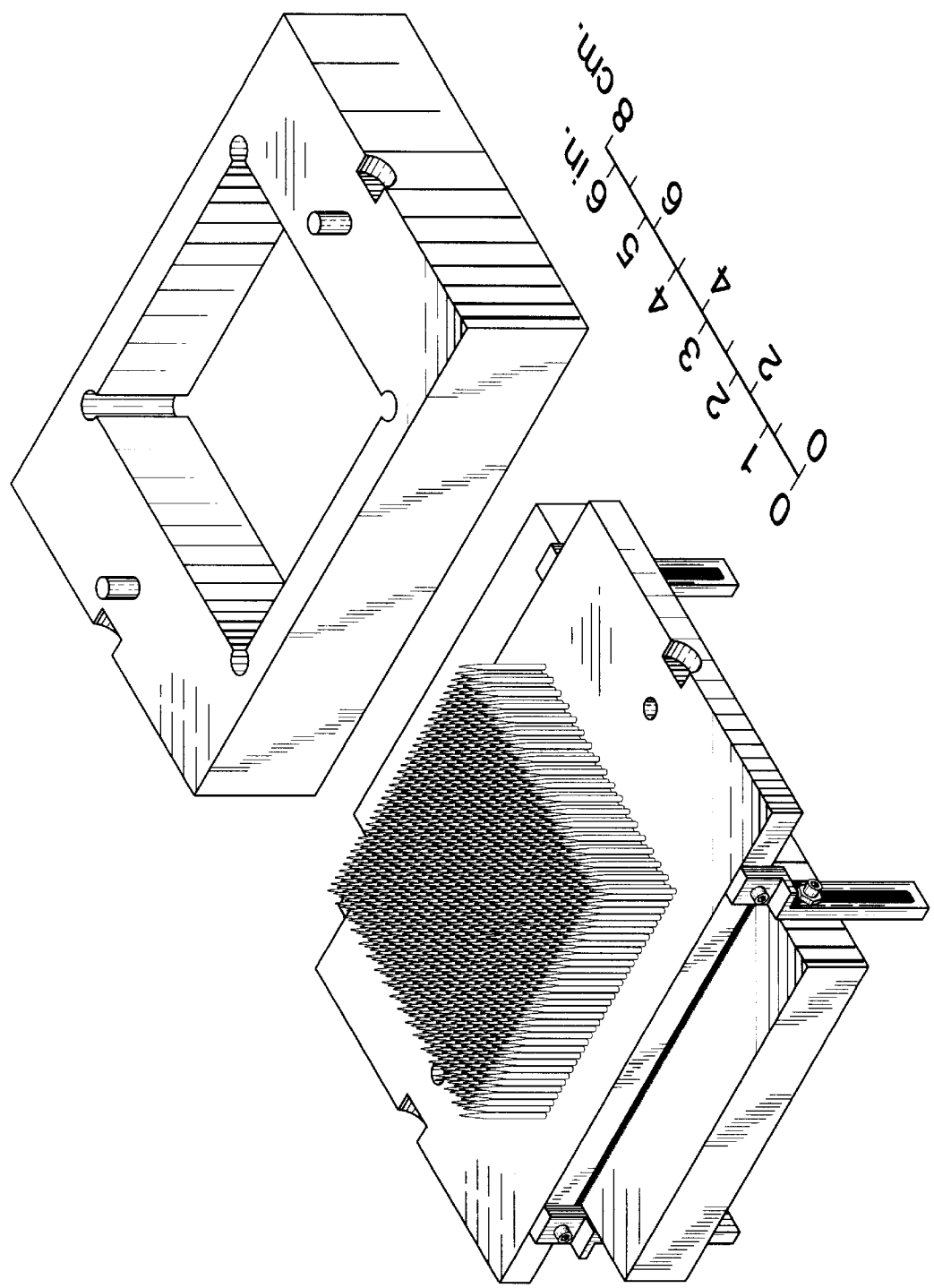
FIG. 1 is a drawing showing the "boat" and "bed-of-nails" mold.

The resulting second mixture or hot melt suspension is quite viscous and must be poured quickly to avoid premature gelling. This second mixture or hot melt is poured into a pre-heated mold or "boat", and a pre-heated mold insert or "bed-of-nails" is lowered into the melt. Both the boat and the bed-of-nails are treated with silicone oil which acts as a mold release agent. The boat and bed-of-nails are shown in FIG. 1. The resulting casting is chilled to about 5° C. to promote gelling of the binder and to form a raw filter material. Once gelled, the raw filter material is removed from the mold and bed-of-nails. Removal of the raw filter material is facilitated with the assistance of a follow plate that is designed into the bed-of-nails. To cross-link and stabilize the raw filter material, it is covered with water that contains less than 5 wt % glutaraldehyde and is allowed to soak for at least 5 days. At the end of the soak period, the raw filter material is heated in the water/glutaraldehyde to 90° C. to complete the cross-linking action. The raw filter material is then frozen and the water freeze-dried out of the raw filter material at about −10° C. using a commercial vacuum freeze dryer.

Following freeze-drying, the resulting raw filter material, now a solid, perforated foam, is heated under vacuum to about 100° C. to remove any residual water. Additional stabilization can be obtained by cross-linking the raw filter material in vapor phase maleic anhydride in a vacuum oven at about 90° C. for several days following freeze drying and vacuum heating just prior to air curing. This is followed by removal of any continuous skin from the raw filter material. It has been found that the raw filter material shrinks during subsequent air curing at elevated temperatures and that the dense skin contributes to distortion as the raw filter material shrinks. Air curing is accomplished by heating the raw filter material in air, starting at about 100° C. and raising the temperature about 10° C. per day up to about 200° C. After several days at about 200° C., the raw filter material shrinks about 20% in the linear dimension and appears dark brown.

The brown, air-stabilized raw filter material is then carbonized under flowing inert gas such as argon or nitrogen by ramping up to and soaking for about 8 hours first at about 500° C. then for about 8 hours at about 100° C. in an inert atmosphere to form an ozone decomposing filter.

Another variation in method that results in slightly more shrinkage of the raw filter material and is slightly more costly is to use propylene glycol as the solvent. About 2 to 30 phs gelatin is dissolved in propylent glycol at about 100° C. to form a first mixture. About 1 phs tannic acid is added to initiate cross-linking of the gelatin. Between about 5 and about 15 phs rayon carbon fibers are then added to the first mixture and tannic acid to form a second mixture, and the second mixture is cast into the boat with the bed of nails as described above and is then chilled to form a raw filter material. Following removal from the mold, the raw filter material is soaked for about 5 days in a soak solution of about 6 times its weight of methanol mixed with less than about 2 wt % glutaraldehyde. The soak solution is exchanged a total of about three times so that the residual propylent glycol in the raw filter material is less than 1%. Following the soak solution exchanges, the raw filter material is heated in the last batch of soak solution to about 50° C. in order to complete the cross-linking with the glutaraldehyde. The methanol is then removed from the raw filter material using supercritical carbon dioxide. Additional vacuum drying, cross-linking, air curing, and carbonization proceed as described above for freeze-dried filters to form an ozone decomposing filter.

The resulting ozone decomposing filter is activated by heating in about 1 cfm flowing carbon dioxide for between about 10 and about 20 hours at about 850° C. Activation can also be done in air at lower temperatures as low as about 350° C.

To determine dimensions for the casting boat and bed-of-nails, calculations may be made using the Hagen-Poiseulle equation (McCabe, Smith, Harriott, Unit Operations of Chemical Engineering, McGraw-Hill, New York, 1976, p. 78) to determine the number of holes and their diameter required to provide desired air flow through the filter with an acceptable pressure. In one embodiment, darning needles were used to make the bed-of-nails. A thin aluminum follow plate was provided to eject the molded casting from the needles in the bed-of-nails mold.

The bed-of-nails, the follow plate, and the boat are assembled and the cavity filled with high flash point silicone oil. The assembly is heated in an oven to about 100° C. prior to casting. The silicone oil is drained out of the boat and from the needles just prior to casting.

TESTING EFFECTIVENESS OF FILTERS AT DECOMPOSING OZONE

Figure 2:
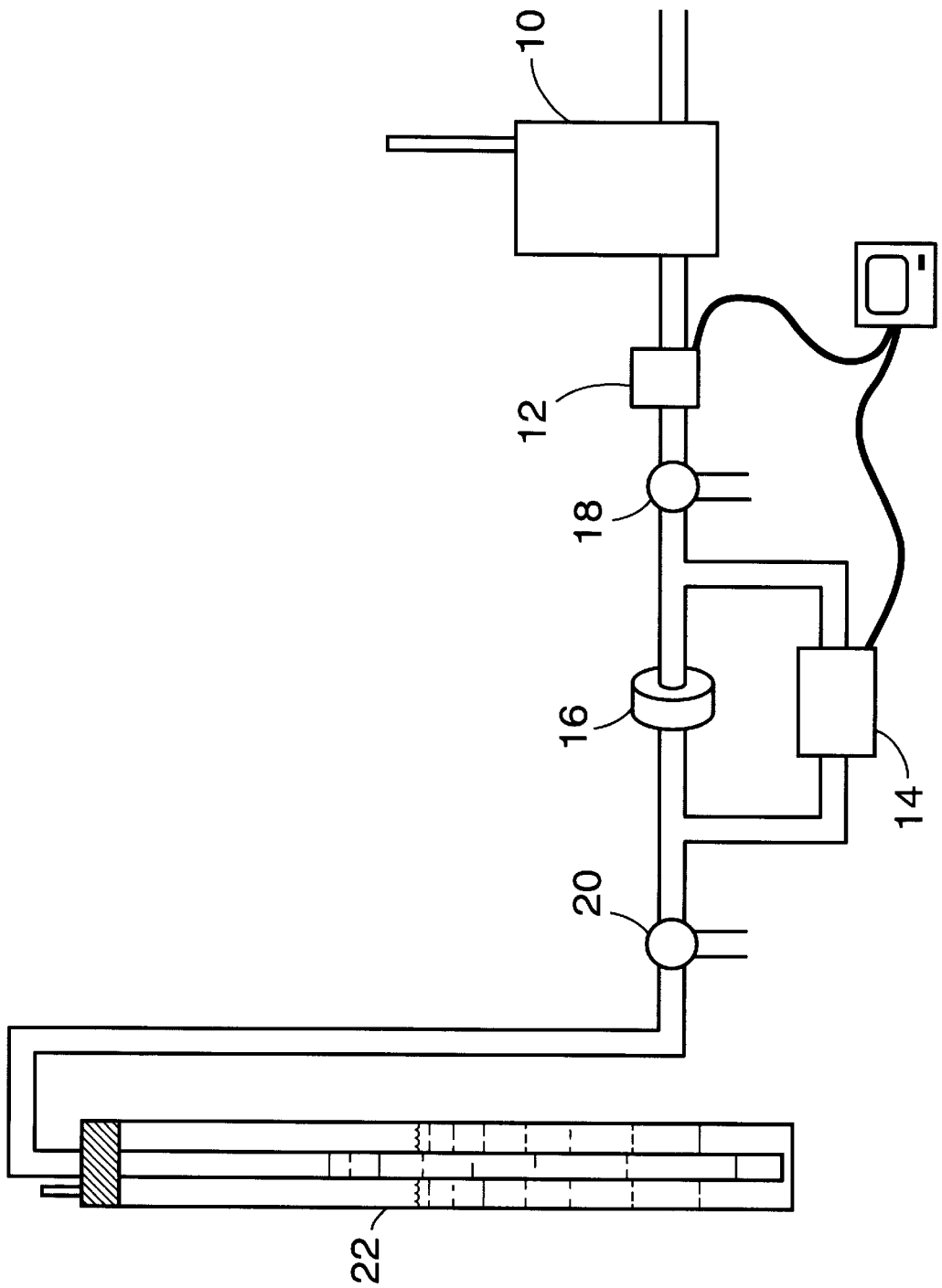
FIG. 2 is a drawing showing the test apparatus for determining the ozone decomposition efficiency and filter back pressure for ozone decomposing filters.

Testing the effectiveness of various ozone decomposing filters was done as follows: A 38 mm diameter disk of the ozone decomposing filter material was cut with a hole saw on a drill press. The sample was loaded into a filter sample holder made of 51 mm diameter plastic heat-shrinkable tubing. A heat gun was used to collapse the plastic tubing around the filter sample and seal it to the ozone testing apparatus. The ozone testing apparatus shown in FIG. 2 consists of an electric discharge ozone generator 10 (Enmet, 0–250 ppm in air), a flow meter 12, a pressure transducer 14, a filter sample holder 16, valves 18 and 20, and a decomposition column 22 (aqueous KI).

For comparison, the ozone decomposition effectiveness of an 18 mm thick sample of a TAK2 (Tokyo Roki) commercially available filter was determined at a variety of flow rates and ozone concentration levels. At a flow rate of 0.5 lpm of air the ozone generator shown in FIG. 2 produces 210 ppm of ozone and less than 0.025 ppm of ozone was detected after passing through the TAK2 filter. At 2.01 pm of air flow, 35 ppm of ozone was produced and 0.1 ppm of ozone was observed after passing through the same TAK2 filter.

EXAMPLE I 120 grams (20 phs) of Aldrich® 300 bloom gelatin were dissolved in 570 grams propylene glycol and 30 grams water at 100° C. to form a first mixture. Then, 7.2 grams (1.2 phs) of tannic acid were dissolved in the first mixture to initiate crosslinking. Upon addition of the tannic acid, the first mixture and tannic acid exothermed to 112° C. 30 grams or 5 phs of carbonized cellulose (rayon) fiber were stirred into the first mixture and tannic acid to form a second mixture, which was then poured into the preheated, mold-released "bed-of-nails" mold. The rayon carbon fibers measured about 10 um diameter by 100 to 500 um long. After chilling the mold and its contents to form a raw filter material, the raw filter material was removed from the mold and bed-of-nails and soaked for 5 days in a soak solution of 2100 grams methanol containing 5.4 grams glutaraldehyde. This soak solution was changed out every 5 to 7 days for a total of three exchanges. At the end of the third exchange, the propylene glycol content of the raw filter material material had been reduced to less than 0.5%. Methanol was then removed from the raw filter material using supercritical carbon dioxide. The raw filter material was heated under 50 mtorr vacuum, then exposed to maleic anhydride vapor at 85° C. for 4 days in a vacuum oven. The maleic anhydride offered additional crosslinking and stabilization. Heating at 104° C. for 7 days under vacuum removed the excess maleic anhydride. The raw filter material was then air cured and stabilized by starting at 100° C. and raising the temperature 10° C. per day until the raw filter material became dark brown at 196° C. Then, any continuous surface skin was removed from the raw filter material, and the raw filter material was carbonized under flowing argon using the following procedure: (1) ramp 3° C./minute to 90° C. (2) Ramp 1° C./min to 200° C. and soak 4 hour, (3) ramp at 1° C./min to 230° C. and soak for 4 hrs, (4) ramp at 1° C./min to 250° C. and soak 4 hrs., (5) ramp at 1° C./min to 295° C. and soak for 4 hours, (6) ramp at 1° C./min to 500° C. and soak for 8hrs, (7) ramp at 2° C./min to 1100° C. and soak for 8 hrs, (8) allow to cool to room temperature to form an ozone decomposing filter Starting with the dry raw filter material after supercritical extraction, this raw filter material experienced approximately 27% linear shrinkage by the time it was carbonized. The ozone decomposing filter was activated twice in 1 cfm flowing carbon dioxide according to the following procedure: ramp 5° C./min to 850° C. and soak 10 hours. The ozone decomposing filter lost 8.3 wt % during this first activation and another 20.4 wt % during the second activation. The following surface area and porosity data were measured: BET surface area=933 $m^2$/gram, 79.5% porosity, bulk density=0.2895 $g/cm^3$, real density=1.42 $g/cm^3$, and average pore diameter=17.5 $\mu$m. Average pore diameters for the corresponding poly(acrylonitrile)-rayon carbon fiber filters were slightly smaller.

The ozone decomposing filter comprised 50.1 wt % rayon carbon fiber and 49.9 wt % gelatin carbon as the binder.

A 11.8 mm thick sample of the ozone decomposing filter described in Example I was evaluated for its ozone decomposition efficiency. At a flow rate of 4.1 lpm the ozone generator produced 37 ppm of ozone. Downstream of the ozone decomposing filter, the amount of ozone present was below the detection limit of the test apparatus (less than 0.025 ppm). At a flow rate of 8.01 lpm (20 ppm ozone produced), only 0.2 ppm of ozone was observed downstream of the ozone decomposing filter.

EXAMPLE II 120 grams (20 phs) of Aldrich® 300 bloom gelatin were dissolved in 570 grams propylene glycol and 30 grams water at 100° C., and 0.6 grams LiBr were added to help dissolve the gelatin and to form a first mixture. Then, 7.2 grams (1.2 phs) of tannic acid were dissolved in the first mixture to initiate crosslinking. 30 grams or 5 phs of carbonized cellulose (rayon) fiber were stirred into the first mixture and tannic acid to form a second mixture, which was then poured into the preheated, mold-released "bed-of-nails" mold. The rayon carbon fibers measured about 10 um diameter by 100 to 500 um long. After chilling the mold and its contents on a −10° C. chill plate to form a raw filter material, the raw filter material was removed from the mold and bed-of-nails and soaked for 8 days in a first soak solution of 2345 grams n-propanol containing 7 grams glutaraldehyde. After 8 days of soaking, the raw filter material was heated to 70° C. in the n-propanol soak solution to complete the crosslinking. The first soak solution was exchanged for a second soak solution of 2300 grams methanol containing 3 grams glutaraldehyde and was soaked for 12 days. At the end of the second exchange, the propylene glycol content of the raw filter material had been reduced to less than 2%. Methanol was then removed from the raw filter material using supercritical carbon dioxide. Any continuous surface skin was then removed from the raw filter material and the raw filter material was heated under 50 mtorr vacuum up to 100° C. for 7 days. This raw filter material did not receive maleic anhydride treatment. The raw filter material was then air cured and stabilized starting at 100° C. and raising the temperature 10° C. per day until the raw filter material became dark brown at 187° C. The raw filter material was carbonized under flowing argon using the following procedure: (1) ramp 3° C./minute to 90° C. (2) Ramp 1° C./min to 200° C. and soak 4 hours, (3) ramp at 1° C./min to 230° C. and soak for 4 hrs, (4) ramp at 1° C./min to 250° C. and soak 4 hrs., (5) ramp at 1° C./min to 295° C. and soak for 4 hours, (6) ramp at 1° C./min to 500° C. and soak for 8 hrs, (7) ramp at 2° C./min to 1100° C. and soak for 8 hrs, (8) allow to cool to room temperature to form an ozone decomposing filter.

Starting with the dry raw filter material after supercritical extraction, this raw filter material experienced approximately 24% linear shrinkage by the time it was carbonized. The resulting ozone decomposing filter was activated in 1cfm flowing carbon dioxide according to the following procedure: ramp 5° C./min to 850° C. and soak 20 hours. The ozone decomposing filter lost 40.2 wt % during this activation.

The ozone decomposing filter comprised 56.3 wt % rayon carbon fiber and 43.7 wt % gelatin carbon as the binder.

A 16.2 mm thick sample of the ozone decomposing filter described in Example II was evaulated for its ozone decomposition efficiency as a function of time at 8.01 lpm (20 ppm). These results are displayed in Table I below. The air was passed through column packed with a color indicating Drierite® drying material before entering the generator. When the color change of the drying column indicated that the drying material was approximately 90% expended, the column was exchanged for a freshly regenerated column. Differences observed with fresh and old columns are noted in the last column of Table I.

TABLE I

| Time of Exposure (Hours) | Ozone Concentration After Filter (ppm) | Condition of Drying Material | % of Ozone Being Destroyed |
|---|---|---|---|
| 0.25 | <0.1 | | |
| 5 | 0.4 | | |
| 12 | 0.5 | | |
| 17 | 0.4 | | |
| 23 | 0.5 | | 97.5 |
| 31 | 0.6 | | |
| 38 | 0.5 | | |
| 45 | 0.9 | | |
| 70 | 0.8 | | |
| 77 | 1.25 | old | |
| 77 | 0.8 | fresh | |
| 100 | 1.2 | | 94 |
| 100 | 0.4 | fresh | |
| 105 | 1.1 | | |
| 125 | 1.3 | old | |
| 132 | 1.8 | | |
| 154 | 2.4 | old | |
| 155 | 1.2 | fresh | |
| 177 | 1.8 | old | |
| 200 | 2.4 | old | |
| 225 | 3.0 | old | |
| 226 | 2.4 | fresh | 88 |

120 grams (20 phs) of Aldrich® 300 bloom gelatin were dissolved in 600 grams water at 80° C., and 0.8 grams LiBr were added to help dissolve the gelatin and to form a first mixture. Then, 7.2 grams (1.2 phs) of tannic acid were dissolved in the first mixture to initiate crosslinking. 30 grams or 5 phs of carbonized cellulose (rayon) fiber were stirred into the first mixture and tannic acid to form a second mixture, which was then poured into the preheated, mold-released "bed-of-nails" mold. The rayon carbon fibers measured about 10 um diameter by 100 to 500 um long. After chilling the casting on a −10° C. chill plate to form a raw filter material, the raw filter material was removed from the mold and bed-of-nails and soaked for 5 days in a soak solution of 1000 grams water containing 6 grams glutaraldehyde. After 5 days of soaking, the filter was heated to 100° C. in the soak solution to complete the crosslinking. The raw filter material was allowed to cool and was frozen at −20° C. in a commercial freeze dryer. After 6 days under 150 mtorr vacuum during which time the temperature of the raw filter material was gradually raised to −7° C., the raw filter material was transferred to a vacuum oven and gradually heated under 75 mtorr vacuum to 92° C. over a period of 4 days. This raw filter material did not receive maleic anhydride treatment. Any continuous surface skin was removed from the raw filter material, and the raw filter material was then air cured and stabilized starting at 100° C. and raising the temperature 10° C. per day until the raw filter material became dark brown at 200° C. The raw filter material was carbonized under flowing argon using the following procedure: (1) ramp 3° C./minute to 90° C. (2) Ramp 1° C./min to 200° C. and soak 4 hours, (3) ramp at 1° C./min to 230° C. and soak for 4 hrs, (4) ramp at 1° C./min to 250° C. and soak 4 hrs., (5) ramp at 1° C./min to 295° C. and soak for 4 hours, ramp at 1° C./min to 500° C. and soak for 8 hrs, (7) ramp at 2° C./min to 1100° C. and soak for 8 hrs, (8) allow to cool to room temperature to form an ozone decomposing filter.

Figure 3:
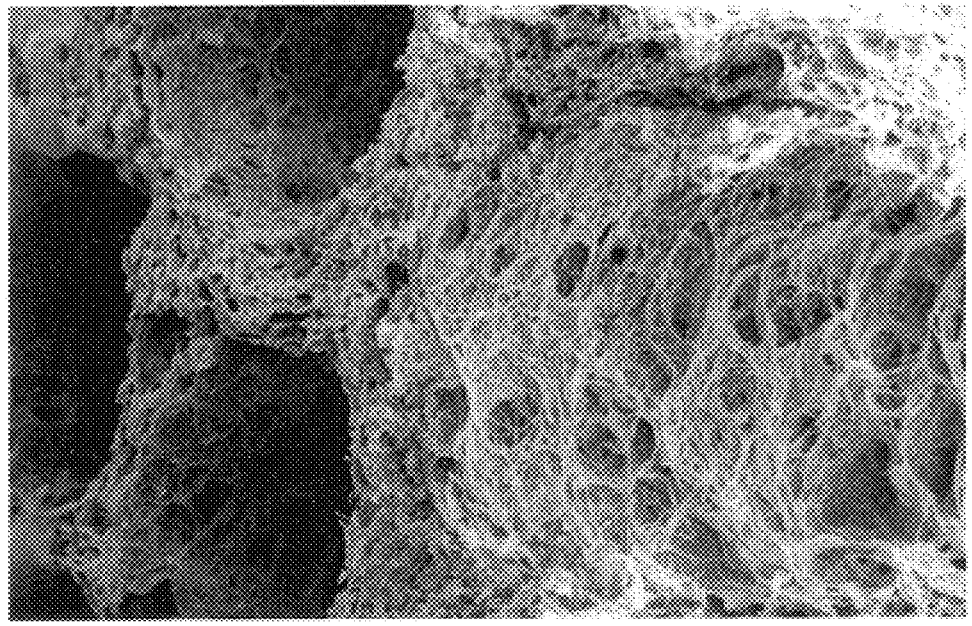
FIG. 3 shows two scanning electron micrographs of the ozone decomposing filter of Example III For a better understanding of the present invention, together with other and further objects, advantages and capabilities thereof, reference is made to the following disclosure and appended claims in connection with the above-described drawings.
Figure 3:
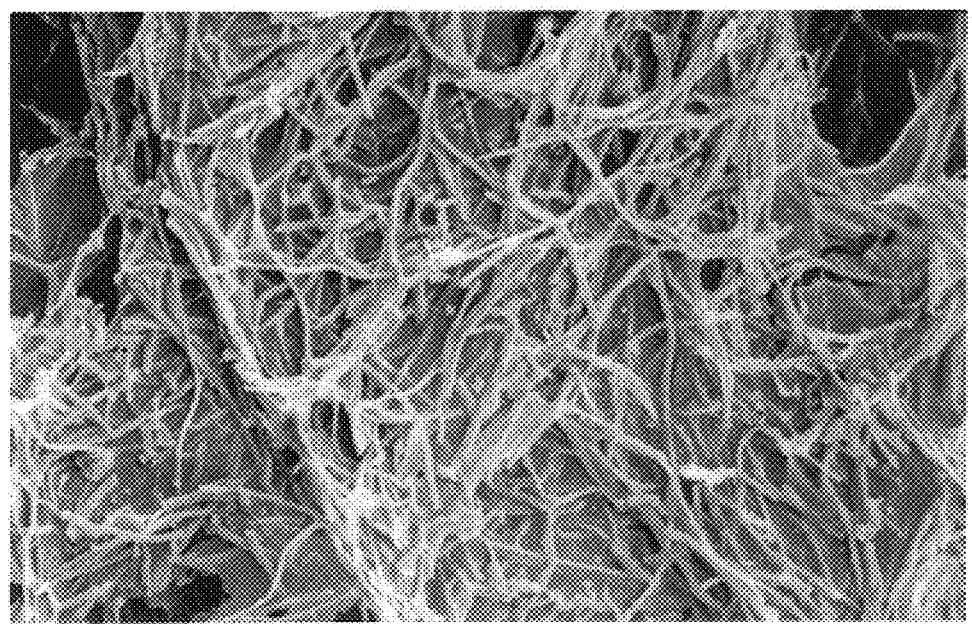

Starting with the dry raw filter material after freeze drying, this raw filter material experienced approximately 6% linear shrinkage by the time it was carbonized. This ozone decomposing filter was activated in 1cfm flowing carbon dioxide according to the following procedure: ramp 5° C./min to 850° C. and soak 15 hours. The filter lost 20.4 wt % during this activation. The following surface area and porosity data were measured on companion ozone decomposing filter scraps: BET surface area=374 $m^2$/gram, 89.3% porosity, bulk density=0.178 $g/cm^3$, real density=1.67 $g/cm^3$, and average pore diameter=24.1 $\mu m$. This is in contrast to poly(acrylonitrile)-rayon carbon fiber filters which had smaller average pore diameters. FIG. 3 shows two scanning electron micrographs of this ozone decomposing filter.

The ozone decomposing filter comprised 53.4 wt % rayon carbon fiber and 46.6 wt % gelatin carbon as the binder.

EXAMPLE IV 120 grams (20 phs) of Aldrich® 300 bloom gelatin were dissolved in 600 grams water at 80° C., and 0.61 grams LiBr were added to help dissolve the gelatin and to form a first mixture. 7.2 grams (1.2 phs) of tannic acid were dissolved in the first mixture to initiate crosslinking. 30 grams or 5 phs of carbonized cellulose (rayon) fiber were stirred into the first mixture and tannic acid to form a second mixture, which was then poured into the preheated, mold-released "bed-of-nails" mold. The rayon carbon fibers measured approximately 10 um diameter by 100 to 500 um long. After chilling the mold and its contents on a −10° C. chill plate to form a raw filter material, the raw filter material was removed from the mold and bed-of-nails and soaked for 4 days in a soak solution of 1000 grams water containing 5 grams glutaraldehyde. After 4 days of soaking, the raw filter material was heated to 100° C. in the soak solution to complete the crosslinking. The raw filter material was allowed to cool and was frozen at −20° C. in a commercial freeze dryer. After 7 days under 150 mtorr vacuum during which time the temperature of the raw filter material was gradually raised to −7° C., the raw filter material was transferred to a vacuum oven and gradually heated under 75 mtorr vacuum to 92° C. over a period of 3 days. This raw filter material did not receive maleic anhydride treatment. Any continuous surface skin was removed from the raw filter material, and the raw filter material was then air cured and stabilized starting at 100° C. and raising the temperature 10° C.) per day until the raw filter material became dark brown at 202° C. The raw filter material was carbonized under flowing argon using the following procedure: (1) ramp 3° C./min to 90° C. (2) Ramp 1° C./min to 200° C. and soak 4 hours, (3) ramp at 1° C./min to 230° C. and soak for 4 (4) ramp at 1° C./min to 250° C. and soak 4 hrs., (5) ramp at 1° C./min to 295° C. and soak hours, (6) ramp at 1° C./min to 500° C. and soak for 8 hrs, (7) ramp at 2° C./min to 1100° C. and soak for 8 hrs, (8) allow to cool to room temperature to form an ozone decomposing filter.

Starting with the dry raw filter material after freeze drying, this raw filter material experienced approximately 9% linear shrinkage by the time it was carbonized. The resulting ozone decomposing filter was activated in 1cfm flowing carbon dioxide according to the following procedure: ramp 5° C./min to 850° C. and soak 15 hours. The ozone decomposing filter lost 22.4 wt % during this activation. The following surface area and porosity data were measured on companion filter scraps: BET surface area=374 m$^2$/gram, 89.3% porosity, bulk density=0.178 g/cm$^3$, real density=1.67 g/cm$^3$, and average pore diameter=24.1 μm. This is in contrast to poly(acrylonitrile)-rayon carbon fiber filters which had smaller average pore diameters. The carbon decomposing filter was machined to 1.4 cm×8.0 cm×8.0 cm and comprised 53.7 wt % rayon carbon fiber and 46.3 wt % gelatin carbon as the binder.

EXAMPLE V 120 grams (20 phs) of Aldrich® 300 bloom gelatin were dissolved in 600 grams water at 77° C., and 0.62 grams LiBr were added to help dissolve the gelatin and to form a first mixture. 7.2 grams (1.2 phs) of tannic acid were dissolved in the first mixture to initiate crosslinking. 30 grams or 5 phs of carbonized cellulose (rayon) fiber were stirred into first mixture and tannic acid to form a second mixture, which was then poured into the preheated, mold-released "bed-of-nails" mold. The rayon carbon fibers measured approximately 10 um diameter by 100 to 500 um long. After chilling the mold and its contents on a −10° C. chill plate to form a raw filter material, the raw filter material was removed from the mold and bed-of-nails and soaked for 7 days in a soak solution of 1000 grams water containing 6 grams glutaraldehyde. After 7 days of soaking, the raw filter material was heated to 100° C. in the soak solution to complete the crosslinking. The raw filter material was allowed to cool and was frozen at −20° C. in a commercial freeze dryer. After 7 days under 150 mtorr vacuum during which time the temperature of the raw filter material was gradually raised to −9° C., the raw filter material was transferred to a vacuum oven and gradually heated under 50 mtorr vacuum to 100° C. over a period of 3 days. This raw filter material did not receive maleic anhydride treatment. Any continuous surface skin was removed from the raw filter material, and the raw filter material was then air cured and stabilized starting at 100° C. and raising the temperature 10° C. per day until the raw filter material became dark brown at 210° C. In order to accelerate the carbonization step, this raw filter material was carbonized under flowing argon using the following procedure: (1) ramp 3° C./minute to 200° C. (2) Ramp 1° C./min to 500° C. and soak 8 hours, (3) ramp at 2° C./minute to 1100° C. and soak for 8 hrs., (8) allow to cool to room temperature to form an ozone decomposing filter. The ozone decomposing filter appeared to be unharmed by this accelerated carbonization.

Starting with the dry raw filter material after freeze drying, this raw filter material experienced approximately 16% linear shrinkage by the time it was carbonized. This ozone decomposing filter was activated in 1 cfm flowing carbon dioxide according to the following procedure: ramp 5° C./min to 850° C. and soak 15 hours. The ozone decomposing filter lost 28.9 wt % during this activation.

The ozone decomposing filter comprised 53.5 wt % rayon carbon fiber and 46.5 wt % gelatin carbon as the binder.

A 15.0 mm thick sample of the ozone decomposing filter of Example V was evaluated for its ozone decomposition efficiency. At a flow rate of 4.0 lpm the ozone generator produced 37 ppm of ozone. Downstream of the ozone decomposing filter, the amount of ozone present was below the detection limit of the instrument (<0.025 ppm). At a flow rate of 8.0 lpm (20 ppm) ozone produced), 0.54 ppm of ozone was observed downstream of the ozone decomposing filter.

EXAMPLE VI 120 grams (20 phs) of Aldrich® 300 bloom gelatin were dissolved in 600 grams water at 80° C., and 0.61 grams LiBr were added to help dissolve the gelatin and to form a first mixture. 7.2 grams (1.2 phs) of tannic acid were dissolved in the first mixture to initiate crosslinking. 30 grams or 5 phs of carbonized cellulose (rayon) fiber were stirred into the first mixture and tannic acid to form a second mixture, which was then poured into the preheated, mold-released "bed-of-nails" mold. The rayon carbon fibers measured approximately 10 um diameter by 100 to 500 um long. After chilling the mold and its contents on a −10° C. chill plate to form a raw filter material, the raw filter material was removed from the mold and bed-of-nails and soaked for 7 days in a soak solution of 1000 grams water containing 6 grams glutaraldehyde. After 6 days of soaking, the raw filter material was heated to 100° C. in the soak solution to complete the crosslinking. The raw filter material was allowed to cool and was frozen at −20° C. in a commercial freeze dryer. After 7 days under 150 mtorr vacuum during which time the temperature of the filter was gradually raised to −9° C., the raw filter material was transferred to a vacuum oven and gradually heated under 50 mtorr vacuum to 100° C. over a period of 3 days. This raw filter material did not receive maleic anhydride treatment. Any continuous surface skin was removed from the raw filter material, and the raw filter material was then air cured and stabilized starting at 100° C. and raising the temperature 10° C. per day until the raw filter material became dark brown at 210° C. In order to accelerate the carbonization step, this raw filter material was carbonized under flowing argon using the following procedure: (1) ramp 3° C./minute to 200° C. (2) Ramp 1° C./min to 500° C. and soak 8 hours, (3) ramp at 2° C./min 1100° C. and soak for 8 hrs., (8) allow to cool to room temperature to form an ozone decomposing filter. The ozone decomposing filter appeared to be unharmed by this accelerated carbonization.

Starting with the dry raw filter material after freeze drying, this raw filter material experienced approximately 16% linear shrinkage by the time it was carbonized. This ozone decomposing filter was activated in 1cfm flowing carbon dioxide according to the following procedure: ramp 5° C./min to 850° C. and soak 15 hours. The ozone decomposing filter lost 30.2 wt % during this activation.

The ozone decomposing filter comprised 51.4 wt % rayon carbon fiber and 48.6 wt % gelatin carbon as the binder.

A 18.1 mm thick sample of the ozone decomposing filter described in Example VI was evaluated for its ozone decomposition efficiency. At a flow rate of 8.0 lpm the ozone generator produced 25 ppm of ozone. Downstream of the ozone decomposing filter, the amount of ozone present was 0.8 ppm after 15 minutes of exposure. After 1.5 hours, approximately 20% of the Drierite column had turned pink and 2.0 ppm of ozone was measured passing through the ozone decomposing filter. The relative humidity was less than 3% throughout the evaluation.

EXAMPLE VII 120 grams (20 phs) of Aldrich® 300 bloom gelatin were dissolved in 600 grams water at 76° C., and 0.6 grams LiBr were added to help dissolve the gelatin and to form a first mixture. 7.2 grams (1.2 phs) of tannic acid were dissolved in the first mixture to initiate crosslinking. 30 grams or 5phs of carbonized cellulose (rayon) fiber and 10.0 grams of ferric oxide pigment were stirred into the first mixture and tannic acid to form a second mixture, which was then poured into the preheated, mold-released "bed-of-nails" mold. The rayon carbon fibers measured approximately 10 um diameter by 100 to 500 um long, and the ferric oxide particulate ranged in diameter from 10 to 80 um. After chilling the mold and its contents on a −10° C. chill plate to form a raw filter material, the raw filter material was removed from the mold and bed-of-nails and soaked for 4 days in a first soak solution of 1000 grams water containing 6 grams glutaraldehyde. After 4 days of soaking, the filter was heated to 90° C. in the first soak solution to complete the crosslinking. The raw filter material was then soaked in a second soak solution of 2300 grams methanol with 4 grams glutaraldehyde for eventual supercritical carbon dioxide extraction. The second soak solution was exchanged once after 7 days, reducing the water content in the raw filter material to approximately 2–3 wt %. The raw filter material was subsequently heated to 50° C. in the second soak solution, then extracted in supercritical carbon dioxide. It was then put into a vacuum oven to remove any residual solvent. After 21 days under 150 mtorr vacuum at 50° C., the raw filter material shrank approximately 25% in length. This filter did not receive maleic anhydride treatment. Any continuous surface skin was removed from the raw filter material, and the raw filter material was then air cured and stabilized starting at 100° C. and raising the temperature 10Co per day until the raw filter material became dark brown at 210° C. In order to accelerate the carbonization step, this raw filter material was carbonized under flowing argon using the following procedure: (1) ramp 3° C./minute to 200° C. (2) Ramp 1° C./min to 500° C. and soak 8 hours, (3) ramp at 2° C./minute to 1100° C. and soak for 8 hrs., (8) allow to cool to room temperature to form an ozone decomposing filter. The ozone decomposing filter appeared to be unharmed by this accelerated carbonization.

Starting with the dry raw filter material after supercritical extraction, this raw filter material experienced a total of approximately 29% linear shrinkage by the time it was carbonized. This ozone decomposing filter was activated in 1 cfm flowing carbon dioxide according to the following procedure: ramp 5° C./min to 850° C. and soak 15 hours. The ozone decomposing filter lost 15.2 wt % during this activation.

The ozone decomposing filter comprised 38.1 wt % rayon carbon fiber, 47.3 wt % gelatin carbon as the binder, and 14.6 wt % ferric oxide catalyst.

A 13.0 mm thick sample of the ozone decomposing filter of Example VII was evaluated for its ozone decomposition efficiency. At a flow rate of 8.0 lpm the ozone generator produced ppm of ozone. Downstream of the ozone decomposing filter, the amount of ozone present was 1.2 ppm after 15 minutes of exposure and a 20% pink Drierite column to dry the air. The relative humidity was less than 3% throughout the evaluation.

EXAMPLE VIII 120 grams (20 phs) of Aldrich® 300 bloom gelatin were dissolved in 600 grams water at 83° C., and 0.6 grams LiBr were added to help dissolve the gelatin and to form a first mixture. Tannic acid was not used for this filter. 15 grams or 2.5 phs of carbonized cellulose (rayon) fiber along with 60.0 grams of Monarch® 1300 (a registered trade mark of Cabot Corporation, Billerica, Mass.) furnace black were stirred into the first mixture to form a second mixture, which was then poured into the preheated, mold-released "bed-of-nails" mold. The rayon carbon fibers measured approximately 10 um diameter by 100 to 500 um long, and the Monarch® 1300 was a high surface area (greater than 560 m$^2$/gram), 13 nanometer furnace black with 9.5 wt % volatile content. After chilling the mold and its contents on a −10° C. chill plate to form a raw filter material, the a raw filter material was removed from the mold and bed-of-nails and soaked in 2000 grams watercontaining 5 grams glutaraldehyde for an extended length of time awaiting repair of the freeze dryer. The raw filter material was heated to 75° C. in the first soak solution to complete the cross-linking. The raw material was frozen at −20° C. in a commercial freeze dryer. After 7 days under 150 torr vacuum in the freeze dryer, the temperature was gradually raised to 100° C. over a period of 3 days under 70 torr vacuum. This raw filter did not receive maleic anhydride treatment. Any continuous skin surface skin was removed from the raw filter material and it was further stabilized in air by heating from 100° C. to 196° C., increasing the temperature 10° C. per day. The resulting dark brown material was carbonized according to the following procedure: (1) ramp 3° C./min to 200° C.; (2) ramp 1° C./min to 300° C. and soak 4 hours; (3) ramp 1° C. /min to 350° C. and soak 4 hours; 1° C./min to 500° C. and soak 8 hrs; (5) ramp 2° C./min to 1100° C. and soak 8 hours. Starting with the dry raw filter material after air stabilizing, the raw filter material experienced approximately 8% linear shrinkage by the time it was carbonized. This filter comprised 85.24% Monarch® P-1300 carbon, 31.3% rayon carbon, and 6.5% gelatin carbon. This filter was not tested for ozone decomposing capabilities.

While there has been shown and described what are at present considered the preferred embodiments of the invention, it will be obvious to those skilled in the art that various changes and modifications can be made therein without departing from the scope of the inventions defined by the appended claims.

We claim:

1. An ozone decomposing filter consisting of an essentially catalyst free, essentially dipentene free porous body consisting of between about 20 wt % and about 80 wt % carbonized cellulosic fibers and between about 80 wt % and about 20 wt % carbonized gelatin.

2. The ozone decomposing filter described in claim 1 wherein said carbonized cellulose fibers comprise carbonized rayon fibers.

3. The ozone decomposing filter described in claim 1 wherein said ozone decomposing filter is perforated.

4. An ozone decomposing filter comprising an essentially catalyst free, essentially dipentene free porous body comprising carbonized cellulosic fibers, carbonized gelatin, and furnace black pigment, the weight proportions of carbonized cellulosic fibers and carbonized gelatin being between about 4:1 and about 1:4; and the proportion of the weight of furnace black pigment to the sum of the weights of carbonized cellulosic fibers, carbonized gelatin, and furnace black pigment being up to about 1:1.

* * * * *